United States Patent
Van Driel et al.

[19]

[11] Patent Number: 5,955,672
[45] Date of Patent: *Sep. 21, 1999

[54] ULTRASONIC BLOOD VOLUME MEASUREMENT IN SOFT-SHELL VENOUS RESERVOIR

[75] Inventors: Michael R. Van Driel, Fountain Valley, Calif.; Darren S. Gray, Grand Junction, Colo.; Victor C. H. Lam; Jill E. Uyeno, both of Honolulu, Hi.; Yu-Tung Wong, Huntington Beach, Calif.

[73] Assignee: Medtronic, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/840,685

[22] Filed: Apr. 29, 1997

[51] Int. Cl.⁶ .................................................... G01F 23/28
[52] U.S. Cl. .............................................. 73/597; 73/149
[58] Field of Search .................. 73/149, 597, 290 V, 73/602; 128/771, DIG. 13

[56] References Cited

U.S. PATENT DOCUMENTS

| | | | |
|---|---|---|---|
| 4,448,207 | 5/1984 | Parrish | 73/861 |
| 4,658,834 | 4/1987 | Blankenship et al. | 73/861.27 |
| 5,299,579 | 4/1994 | Gedeon et al. | 128/719 |
| 5,303,585 | 4/1994 | Lichte | 73/149 |
| 5,458,566 | 10/1995 | Herrig et al. | 73/862.634 |

FOREIGN PATENT DOCUMENTS

WO86/06606  11/1986  WIPO.
WO94/21311  4/1994  WIPO.

OTHER PUBLICATIONS

"Bladder Scan Technology"—promotional literature of Diagnostic Ultrasound Corp. (DOC #900–0110 01 85).
"The Accuracy of Portable Ultrasound Scanning in the Measurement of Residual Urine Volume", The Journal of Urology, vol. 152, Dec. 1994.
COBE Corp. literature: Appendix C: COBE CMS Bracket for CMS VRB–1200, pp. 46 & 47, date unknown.

*Primary Examiner*—Hezron Williams
*Assistant Examiner*—Nashmiya Fayyaz
*Attorney, Agent, or Firm*—Harry G. Weissenberger

[57] ABSTRACT

Blood volume in a soft-shell venous reservoir is measured for real-time display by ultrasonically measuring the distance between the walls of the reservoir bag at representative points and determining the volume of the bag by an interpolation based on the known shape of the reservoir bag as it expands and contracts.

7 Claims, 2 Drawing Sheets

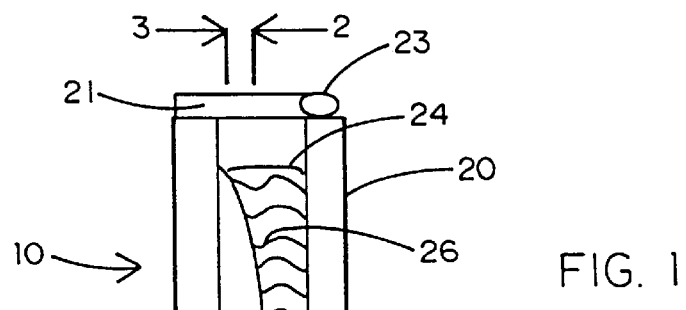
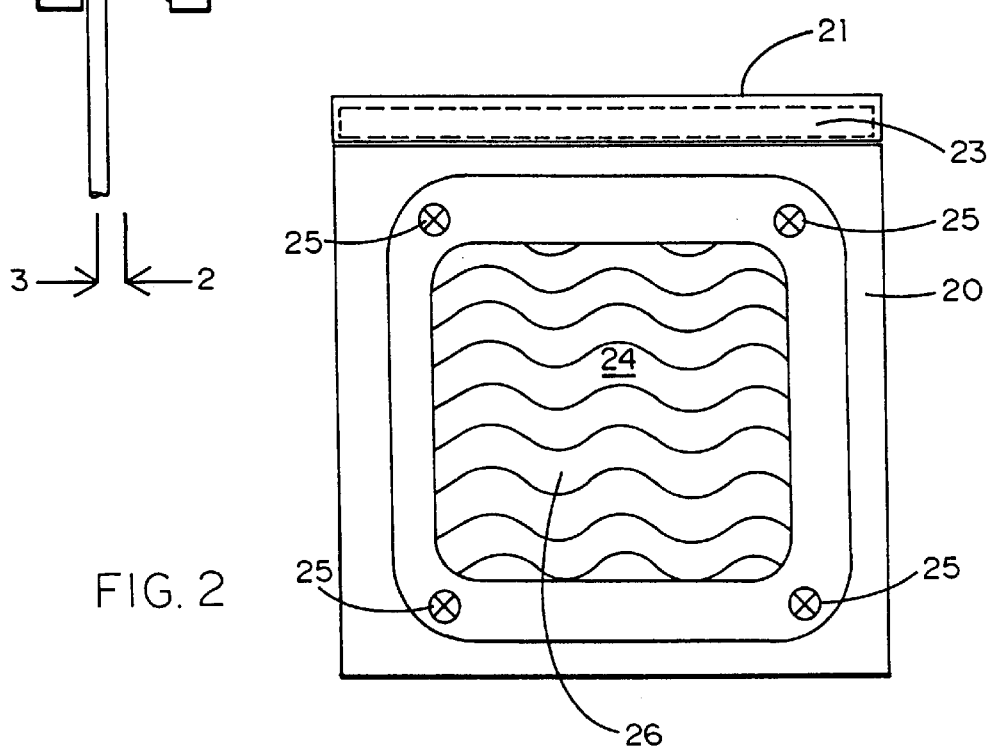

ULTRASONIC BLOOD VOLUME MEASUREMENT IN SOFT-SHELL VENOUS RESERVOIR

FIELD OF THE INVENTION

This invention relates to the measurement of the blood volume in a soft-shell venous reservoir of a heart-lung machine, and more particularly to a method and apparatus using ultrasonic measurement of the width variations of the reservoir to track blood volume variations.

BACKGROUND OF THE INVENTION

Heart-lung machines conventionally include a venous reservoir which receives the patient's blood at a variable rate during open-heart surgery and releases it at a substantially steady rate to the oxygenation circuit from which it is returned to the patient. In the operation of the heart-lung machine, it is important for the perfusionist to be continuously advised of the exact volume of blood in the reservoir, as this information is needed to maintain the correct diluted blood volume in the patient and to calculate the proper doses of infused drugs.

Rigid hard-shell reservoirs lend themselves well to this purpose because accurate graduations can readily be inscribed on their surface. However, because the volume of the hard-shell reservoir itself is constant, it will discharge potentially lethal air into the blood circuit of the heart-lung machine if it is allowed to become empty.

Collapsible soft-shell reservoirs (i.e. plastic bags) have the advantage of increasing and reducing their volume in accordance with the amount of blood they contain, and they consequently need no airspace that could produce emboli. On the other hand, soft-shell reservoirs, because they are always exactly filled with blood, cannot provide a visible volume indication by way of graduations.

In the past, perfusionists have estimated the blood volume in soft-shell reservoirs by the appearance of the reservoir bag, but this requires experience and is not sufficiently accurate for modern requirements. To remedy this deficiency, it has previously been proposed to position the reservoir bag between two parallel plates which are biased against the bag, and whose distance from each other as the bag expands and contracts is indicated by a tape measure. That system, however, is not very accurate and is awkward to observe. Ultrasonic volume measurement has been proposed in the form of an ultrasound image scan of a patient's abdomen to calculate the volume of urine in the patient's bladder, but this procedure can only produce approximate results and would not be suitable for venous reservoir evaluation.

There consequently remains a need for a system which can provide a substantially exact measurement of the fluid volume in a soft-shell venous reservoir on a continuing basis.

SUMMARY OF THE INVENTION

The present invention fills the above need by using ultrasound to locate the walls of the reservoir bag and to provide an indication of the distance between them at representative points on the surface of the bag. The readings at these points can be interpolated and integrated by a microprocessor to provide a volume indication that can be digitally displayed on a monitor.

BRIEF DESCRIPTION OF THE DRAWINGS

FIG. 1 is a side elevation of the reservoir bag and transducer portion of a preferred embodiment of the invention;

FIG. 2 is a section along line 2—2 of FIG. 1; and

DESCRIPTION OF THE PREFERRED EMBODIMENT

Figure 3:
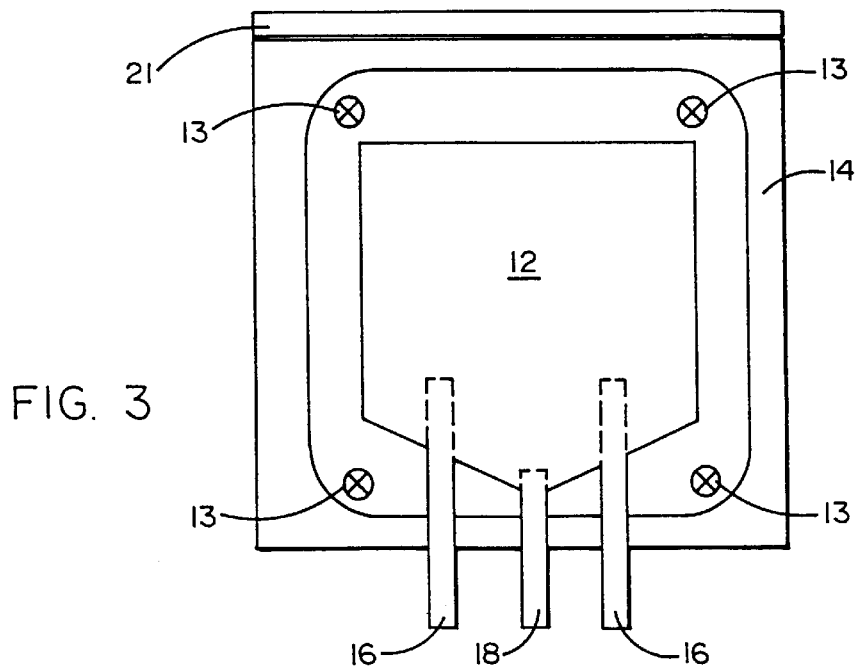
FIG. 3 is a section along line 3—3 of FIG. 1.

FIGS. 1–3 show the structural portion 10 of the present invention. A plastic sheet whose central section forms an expandable soft-shell venous reservoir bag 12 is firmly attached at 13 (FIG. 2) against the backplate 14 of a reservoir holder which may conveniently be mounted on an IV stand (not shown) or the like.

Inlet connectors 16 and an outlet connector 18 extend into the bag 12 to convey blood into and out of the bag 12.

A transducer unit 20 is so mounted with respect to the backplate 14 as to be biased toward it, and consequently toward the bag 12, as indicated by the arrow 22. This may be accomplished by mounting the transducer unit 20 on an arm 21 for pivotal movement about a spring-loaded hinge 23. The transducer unit 20 has attached to its active face at 25 (FIG. 3) a flexible container 24 of acoustically conductive gel 26 which is in contact with both the transducers of transducer unit 20 and the surface of the bag 12. The gel material 26 is sufficiently fluid to allow the flexible container 24 to follow the deformation of, and remain in contact with, the surface of bag 12 as blood is introduced and discharged through the connectors 16, 18 at varying rates. The venous reservoir bag 12 does not expand by more than about 1.5 cm between its empty and full conditions, so that little deformation of the gel layer occurs. Preferably, the bag 12 is formed of a material such as polyvinyl chloride, which is flexible yet provides a strong ultrasonic echo.

The transducer unit 20 may take various forms. In the preferred embodiment, however, the unit 20 consists of a two-dimensional array of transducers disposed to face strategic points on the surface of the bag 12. In this respect, it should be noted that the bag 12, when filled with blood, will expand in a rather uniform geometric shape, so that the shape of the bag can be accurately interpolated from relatively few reference points (and hence few transducers). The number of reference points necessary for an accurate shape determination will vary depending upon the structure and shape of a particular model of bag 12.

Figure 4:
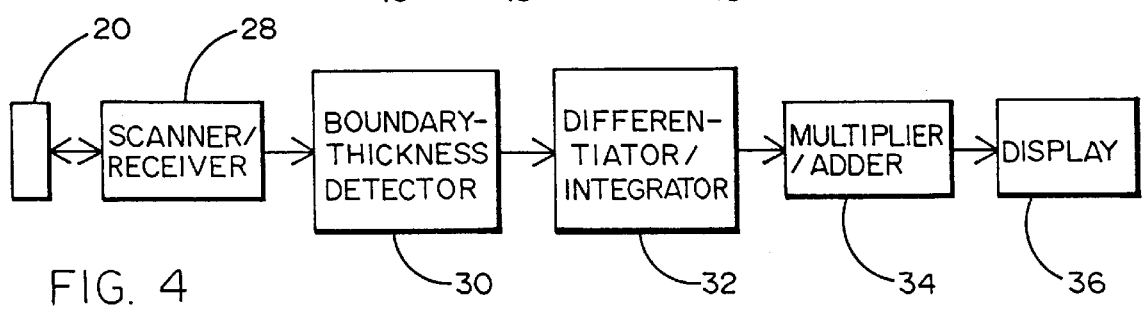
FIG. 4 is a block diagram showing the determination of blood volume from the ultrasonic scan.

FIG. 4 shows, in schematic form, the derivation of the volume indication in the apparatus of this invention. The transducer array 20 is continually sequentially driven and read by a scanner/receiver 28. A boundary/thickness detector 30 locates the peaks in the received echo that identify the walls of the bag 12 and computes the distance between the walls from the time difference between the echo peaks. This information is then applied to a differentiator/integrator 32 which determines the cross-sectional area of the bag 12 between array elements in the manner described below. A multiplier/adder 34 uses the output of differentiator/integrator 32 at various scan points to compute the volume of bag 12 in real time, and the result can be displayed on a digital volume display 36.

Because the surface of the bag 12, as it fills, assumes a predictable curvature at representative points on the surface, and because that curvature is a function of the distance between the walls of the bag 12 at those points, it is possible to accurately calculate the variation of dz/dx (where z is the distance between the walls of the bag 12 and x is the horizontal position) between two rather widely spaced horizontally adjacent points. By integrating this function between the two points, the horizontal cross-sectional area of the bag 12 between the two points can be computed. By performing the same calculation in the vertical direction and multiplying the results, increments of volume can be accurately calculated and added to provide the total volume in the bag 12.

Figure 5:
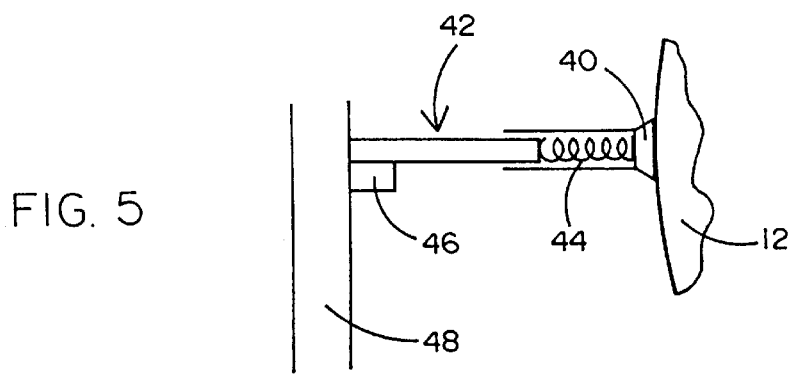
FIG. 5 is a schematic elevation of an alternative embodiment of the invention.

In another preferred embodiment of the invention shown in FIG. 5, the transducer unit 20 is replaced by a traveling transducer or horizontal transducer array 40 which may be mounted on a telescoping arm 42. A spring 44 may be used to bias the transducer 40 against the bag 12, and a motor 46 may be used to move the arm 42 up and down on a pole 48. The signal obtained by a pass of the transducers along the center of the bag 12 represents the vertical section of the bag 12 having the maximum expansion. Knowing the shape of the bag, this representation can be translated into a volume indication.

It is understood that the exemplary ultrasonic measurement of blood volume in soft-shell venous reservoirs described herein and shown in the drawings represents only presently preferred embodiments of the invention. Indeed, various modifications and additions may be made to such embodiment without departing from the spirit and scope of the invention. For example, in the embodiment of FIG. 1, the ultrasound emitter or emitters may be in the unit 20 while the receivers are in the backplate 14. Thus, other modifications and additions may be obvious to those skilled in the art and may be implemented to adapt the present invention for use in a variety of different applications.

We claim:

1. A method of measuring the blood volume in an expandable soft-shell blood reservoir having a pair of substantially parallel flexible side walls which normally lie against each other but one of which expands convexly away from the other in a predetermined curvature as blood is introduced therebetween to form an airless blood container, comprising the steps of:

a) mounting said reservoir on a backplate;

b) filling said reservoir with blood so as to cause said one of said walls to expand away from said other wall;

c) ultrasonically measuring the distance between said walls of said reservoir at predetermined discrete points on said reservoir;

d) interpolating said distance measurements between said points in accordance with said predetermined curvature of said one of said walls as it expands away from said other wall; and e) translating said measured and interpolated distance measurements into a displayable measurement of the volume encompassed by said walls.

2. The method of claim 1, in which said measuring step includes the steps of:

i) applying ultrasonic transducing apparatus in sound-transmitting relationship against said one of said walls of said reservoir;

ii) obtaining ultrasonic echoes from said walls of said reservoir; and iii) using said echoes to monitor the distance between said walls of said reservoir at said discrete points.

3. The method of claim 2, in which said ultrasonic transducing apparatus is a transducer array substantially parallel to said other wall of said reservoir.

4. The method of claim 1, in which said transducing apparatus is a movable transducer arranged to travel along said one of said walls of said reservoir to measure the distance between said walls at said discrete points.

5. A system for measuring blood volume stored in a blood circuit, comprising:

a) a soft-shell reservoir for storing blood in said circuit, said reservoir having a pair of ultrasound-reflective walls, and said reservoir being expandable and collapsible so as to always have a volume equal to the volume of blood stored in said reservoir;

b) a backplate for mounting said reservoir, said backplate engaging one of said walls;

c) ultrasonic transducing apparatus arranged to be biased in sound transmitting relationship against the other of said walls of said reservoir opposite said backplate, and to continually provide an indication of the distance between said walls at discrete points on said other of said walls of said reservoir; and d) computing apparatus arranged to compute from said indication a displayable real-time measurement of the volume of said reservoir.

6. The system of claim 5, in which a flexible container of a sound-transmitting gel is interposed between said transducing apparatus and said other of said walls of said reservoir so as to maintain said transducing apparatus in sound-transmitting contact with said other of said walls as said reservoir expands and contracts.

7. The system of claim 5, in which said transducer apparatus is a transducer mounted for movement along said other of said walls of said reservoir.

* * * * *